United States Patent [19]

Martin et al.

[11] Patent Number: 4,788,852

[45] Date of Patent: Dec. 6, 1988

[54] METERING CHOKE

[75] Inventors: Wallace W. Martin; Douglas I. Exall, both of Calgary, Canada; Toshimasa Tomoda; Shinji Badono, both of Tokyo, Japan

[73] Assignees: Petro-Canada Inc., Calgary, Canada; Mitsubishi Electric Corp., Tokyo, Japan; a part interest

[21] Appl. No.: 935,677

[22] Filed: Nov. 28, 1986

[30] Foreign Application Priority Data

Nov. 27, 1985 [CA] Canada .................................. 496346

[51] Int. Cl.[4] .......................................... G01N 11/00
[52] U.S. Cl. ................. 73/61.1 R; 73/861.04
[58] Field of Search ............ 73/61.1 R, 61 R, 861.04; 378/53; 250/301

[56] References Cited

U.S. PATENT DOCUMENTS

| | | | |
|---|---|---|---|
| 2,833,929 | 5/1958 | Barieay | 378/53 |
| 3,033,036 | 5/1962 | Leisey | 73/861.04 |
| 3,496,558 | 2/1970 | Willson et al. | 73/28 |
| 3,746,874 | 7/1973 | Ohata et al. | 378/53 |
| 3,934,471 | 1/1976 | White et al. | 73/861.04 |
| 4,064,440 | 12/1977 | Roder | 250/359 |
| 4,228,353 | 10/1980 | Johnson | 73/861.04 |
| 4,458,524 | 7/1984 | Meador et al. | 73/61.1 R |
| 4,580,441 | 4/1986 | Sakurai et al. | 73/28 |

FOREIGN PATENT DOCUMENTS

| | | | |
|---|---|---|---|
| 3035929 | 4/1982 | Fed. Rep. of Germany . | |
| 103616 | 6/1983 | Japan | 73/861.04 |
| 151517 | 9/1983 | Japan | 73/861.04 |
| 2083908 | 3/1982 | United Kingdom . | |
| 2088050 | 6/1982 | United Kingdom . | |

Primary Examiner—Stewart J. Levy
Assistant Examiner—Hezron E. Williams
Attorney, Agent, or Firm—William R. Hinds

[57] ABSTRACT

The gas and water content of crude oil flowing through a pipeline is measured using a flow restriction in the pipeline, a radioactive source for providing separate radiation energies for each component to be measured, a detector for detecting the radiation transmitted by the various components to generate a first set of signals, pressure gauges upstream of and in the flow restriction for providing a second set of signals, and a signal processor for correlating the signals to provide mass flowrate values indicative of the relative proportions of the components of the mixture. The temperature of the mixture in the flow restriction can also be measured and fed to the signal processor for ensuring that accurate values of flowrate are obtained when temperatures vary.

8 Claims, 1 Drawing Sheet 4,788,852

METERING CHOKE

BACKGROUND OF THE INVENTION

This invention relates to the measuring of the gas and/or water content of oil, and in particular to a method and apparatus for measuring the proportions of gas, water and oil in a crude oil flowing mixture.

The production of oil through wells and production pipelines is usually accompanied by the production of some associated gas or water. The measurement of the volume fractions of such components in the flowing system is of importance in any oil production system, but particularly in the case of offshore production where several wells may be connected to a subsea manifold with one riser or pipeline to the surface. A knowledge of the oil, water and gas components in the pipeline from each well would provide information needed for better control of a production system and the producing reservoir.

Several techniques exist for measuring one or more of these components. For example, capacitance or microwave techniques are used to measure water content in a flowing pipeline; gamma-ray or neutron techniques can be used to measure the void or gas fraction.

Another method involves the use of an oil/water separator for measuring the volume of water in crude oil. However, such a method measures the quantity of water by batch only. In crude oil, water and oil are often emulsified, in which case separation is incomplete which results in erroneous measurements. Moreover, the quantity of gas in the oil must be measured separately, and since regulatory bodies usually require individual well flow measurements on a frequent basis, a separate test separator is needed for this purpose. Since the oil/water separator is large, and occupies precious space on a production or drilling platform, there exists a need for a reliable method of measuring the proportions of gas and water in flowing crude oil from an individual well or combined well flow. The object of the present invention is to meet such a need.

SUMMARY OF THE INVENTION

Accordingly, the present invention relates to a method of measuring the proportions of various components in a crude oil mixture flowing through a pipeline comprising the steps of irradiating said mixtures with gamma rays or x-rays of at least three distinct energy levels; detecting the gamma rays or x-rays of at least three distinct energy levels passing through a known volume of the mixture to generate at least three signals proportional to said components in the mixture; processing said signals to obtain a mass ratio of the components; measuring the temperature of the mixture; measuring the pressure drop of the mixture through a flow restriction; and correlating the mass ratio, temperature and pressure drop values and standard calibration correlations previously prepared to obtain a mass flow rate of each of the components present in the mixture. Preferably the irradiating step is performed in the flow restriction.

The standard calibration correlations are independently measured pressure drop data for various mixtures of oil, water and gas systems, with or without other components such as sand, flowing through a flow restriction with the same geometry as used in the instrument.

The invention also relates to an apparatus for measuring the proportions of various components in a crude oil mixture flowing in a pipeline comprising a choke means for restricting the flow of a mixture along a predetermined length of the pipeline; a source of radioactivity for irradiation the mixture in the area of said choke means with gamma rays or x-rays of at least three distinct energy levels; detector means for detecting the gamma rays or x-rays of at least three distinct energy levels transmitted by the components of said mixture to generate a first set of signals, pressure measuring means for measuring the pressure drop of said mixture across said choke means to generate a second set of signals; and signal processor means for correlating the first and second set of signals and standard calibration correlations previously prepared to provide a mass flow rate for the mixture indicative of the relative proportions of each of the components of the mixture. Preferably the source of radio activity and the detector means are located in the choke means. The apparatus may also include temperature gauge means for measuring the temperature of the mixture in the area of the choke means to generate a third set of signals for correlation with the first and second set of signals. In a preferred embodiment, the choke means is variable for changing the size of the restriction on the flow of the mixture.

BRIEF DESCRIPTION OF THE DRAWINGS

The invention will now be described in greater detail with reference to the accompanying drawing, which illustrates two embodiments of the invention, and wherein.

DESCRIPTION OF THE PREFERRED EMBODIMENTS

Figure 1:
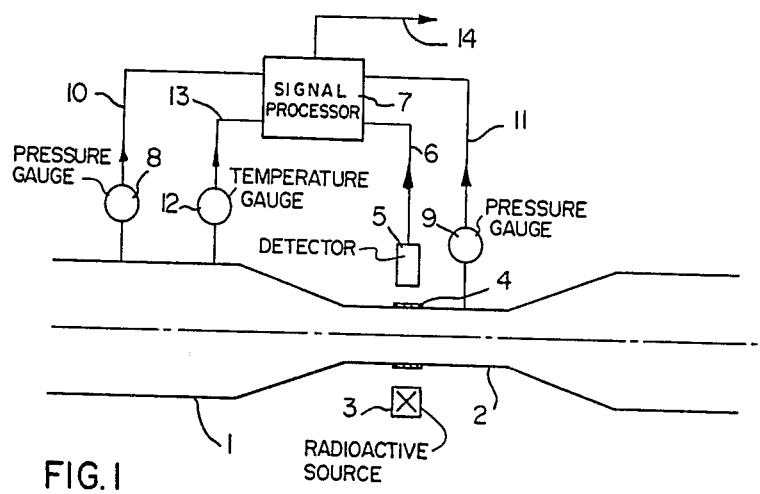
FIG. 1 is a schematic, longitudinal sectional view of a pipeline incorporating one embodiment of the apparatus of the present invention.

With reference to the drawing and in particular FIG. 1, the apparatus of the present invention is intended for use in a pipeline 1 carrying crude oil, water and gas either as a distributed mixture, stratified, or a combination thereof. The apparatus is incorporated into a choke section 2 of the pipeline 1, and includes a source 3 of radioactivity, i.e. γ or x-rays. A low absorption window 4 may be incorporated into the choke section 2 of the pipeline to increase the transmission of radiation through the crude oil. Radiation transmitted by the oil across the pipeline 1 is detected by a detector 5, and fed via line 6 to a signal processor 7.

At the same time the pressure drop across the choke section 2 is measured using pressure gauges 8 and 9. Signals generated by the pressure gauges 8 and 9 are fed through lines 10 and 11, respectively to the signal processor 7. The temperature of the crude oil is measured using a gauge 12, which produces an additional signal for transmission to the processor via line 13. The processor 7, which may be a microcomputer, provides a signal which is transmitted via an output line 14 to a display unit (not shown), which provides a visual indication of the oil, gas and water flowrates in the crude oil stream.

Figure 2:
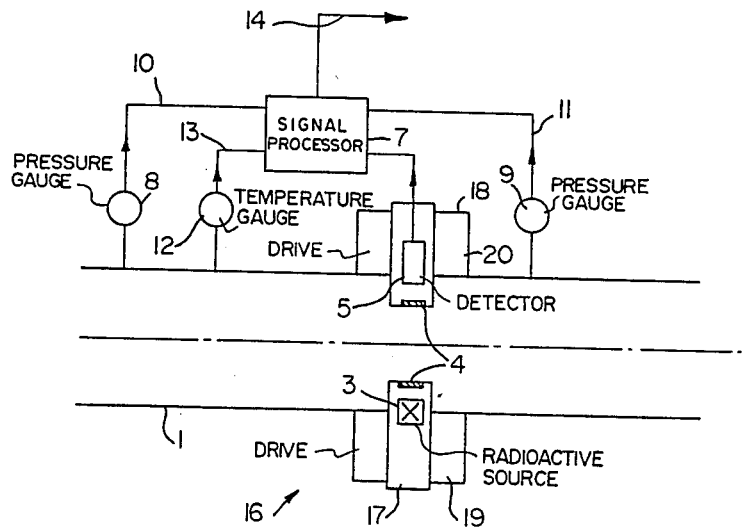
FIG. 2 is a schematic, longitudinal sectional view of a pipeline incorporating a second embodiment of the apparatus of the present invention.

The apparatus of FIG. 2 is virtually identical to that of FIG. 1, and accordingly, wherever possible, the same reference numerals have been used to identify the same or similar elements.

With reference to FIG. 2, the choke section 2 of the pipeline 1 can be replaced by a variable choke section generally indicated at 16. The variable choke section 16 is defined by a pair of casings 17 and 18 carrying the source 3 of radioactivity and the detector 5, respectively, and drive elements 19 and 20 for moving the casings 17 and 18 towards or away from each other. The drive elements 19 and 20 may, for example be fluid actuated cylinders, with piston rods carrying the casing 17 and 18.

In operation, the detector 5 detects the radiation transmitted through the fluids in the choke section 2 or 16 of the pipeline 1. The source of radiation 3 actually contains a source providing $\gamma$ or x-rays of at least three distinct energy levels or, alternatively, separate and distinct sources for irradiating the fluid in the pipeline 1. In the case where the radiation beam path length through the mixture is fixed, invariable and known, only two different photon energies are required for determination of 3 components in the mixture. The detector 5 contains one or more separate radiation measuring elements capable of distinguishing different energy levels of $\gamma$ or x-radiation. The radiation source(s) and measuring element(s) are designed to provide signals indicative of the quantity of radiation transmitted by the three separate components of the mixture in the pipeline 1.

The signal processor 7 includes a preamplifier (not shown) which amplifies the pulse signals sent from the radiation detector 5. The amplified signals are passed to an amplifier to further amplify the signals, which are then fed into three pulse-height discriminators. The discriminators fix the window levels corresponding to two photon energies. An arithmetic processor receives the pulse-height discriminator output, and calculates the mass ratios of oil, water and gas in the crude oil which are proportional to the logarithm of the intensity of transmitted radiation. The pressure drop values provided by the gauges 8 and 9 are correlated with the mass ratio values in the arithmetic process and compared with standard calibration correlations stored in the processor to provide mass flow rates of the oil, water and gas components of the crude oil. The results are fed to a display unit. Since the fluid densities are in general temperature dependent, the temperature measurements fed to the signal processor 7 permit accurate calculation of the mass flow rates when compared to reference values.

The radiation detector 5 can be a gas charged, proportional counter tube. The measuring instruments such as the preamplifier, amplifier and pulse-height discriminator are off-the-shelf items commonly used for radiation measurement. The arithmetic processor can be a microcomputer or an analog circuit.

Attenuation of radiation in any material can be expressed as follows:

$$\ln I_o/I = \mu \rho d$$

where $I_o$ is the intensity of the incident radiation, I is the intensity of transmitted radiation, $\mu$ is the radiation mass absorption coefficient of the material, $\rho$ is the density of the material and d is the transmission length in the material. If the radiation transmission distance in the crude oil-gas-water stream is D(cm), the total length of the oil constituent is $d_o$, the total length of the water constituent is $d_w$, the total length of the gas constituent is $d_g$, $\mu_o$, $\mu_w$, and $\mu_g$ are the radiation mass absorption coefficients of oil, water and gas, respectively. $\rho_o$, $\rho_w$, and $\rho_g$ are the density of the oil, water, gas, respectively, $I_o$ and I are the intensity of the incident radiation and the intensity of the transmitted radiation, respectively, d/2 is the thickness of the pipe wall in which measurement occurs, $\rho$ is the density of the pipe wall in the measured portion, $\mu$ is the radiation mass absorption coefficient of the portion of the pipe wall where measuring occurs, then the following equations can be obtained.

$$\mu_{o1}\rho_o d_o + \mu_{w1}\rho_w d_w + \mu_{g1}\rho_g d_g = \ln(I_{o1}/I_1) - \mu_1 \rho d \quad (1)$$

$$\mu_{o2}\rho_o d_o + \mu_{w2}\rho_w d_w + \mu_{g2}\rho_g d_g = \ln(I_{o2}/I_2) - \mu_2 \rho d \quad (2)$$

$$\mu_{o3}\rho_o d_o + \mu_{w3}\rho_w d_w + \mu_{g3}\rho_g d_g = \ln(I_{o3}/I_3) - \mu_3 \rho d \quad (3)$$

The subscripts 1, 2 and 3 relate to the three distinct energies of irradiation. Since $\mu_1 \rho d$ is constant and $I_{o1}$ can be determined in advance, the right-hand-side of the equation in each case can be determined by measuring the intensity of the transmitted radiation. If the transmitted radiation is $C_1$, i.e.

$$\ln(I_{o1}/I_1) - \mu_1 \rho d = \ln I_{o1} - \mu_1 \rho d - \ln I_1 = a_1 - \ln I_1 = C_1 \quad (4)$$

and similarly, $$\ln(I_{o2}/I_2) - \mu_2 \rho d = \ln I_{o2} - \mu_2 \rho d - \ln I_2 = a_2 - \ln I_2 = C_2 \quad (5)$$

$$\ln(I_{o3}/I_3) - \mu_3 \rho d = \ln I_{o3} - \mu_3 \rho d - \ln I_3 = a_3 - \ln I_3 = C_3 \quad (6)$$

can be obtained.

Since radiation energies are selected to make $\mu_{o1}$, $\mu_{w1}$, $\mu_{g1}$, $\mu_{o2}$, $\mu_{w2}$, $\mu_{g2}$, and $\mu_{o3}$, $\mu_{w3}$, $\mu_{g3}$ linearly independent of one another, equations (1), (2) and (3) can be solved for $d_o \rho_o$, $d_w \rho_w$, $d_g \rho_g$ as follows:

$$d_o \rho_o = N_o/M \quad (7)$$

$$d_w \rho_w = N_w/M \quad (8)$$

$$d_g \rho_g = N_g/M \quad (9)$$

where $$M = \mu_{o1}\mu_{w2}\mu_{g3} + \mu_{g1}\mu_{o2}\mu_{w3} + \mu_{w1}\mu_{g2}\mu_{o3} - \mu_{o1}\mu_{g2}\mu_{w3} - \mu_{g1}\mu_{w2}\mu_{o3} - \mu_{w1}\mu_{o2}\mu_{g3} \quad (10)$$

$$N_o = C_1\mu_{w2}\mu_{g3} + C_2\mu_{g1}\mu_{w3} + C_3\mu_{w1}\mu_{g2} - C_1\mu_{g2}\mu_{w3} - C_2\mu_{g1}\mu_{w2} - C_3\mu_{w1}\mu_{g3} \quad (12)$$

$$N_w = C_1\mu_{g2}\mu_{o3} + C_2\mu_{o3}\mu_{g3} + C_3\mu_{g1}\mu_{o2} - C_1\mu_{o2}\mu_{g3} - C_2\mu_{g1}\mu_{o2} - C_3\mu_{o1}\mu_{g2} \quad (11)$$

$$N_g = C_1\mu_{o2}\mu_{w3} + C_2\mu_{w1}\mu_{o3} + C_3\mu_{o1}\mu_{w2} - C_1\mu_{w2}\mu_{o3} - C_2\mu_{o1}\mu_{w3} - C_3\mu_{w1}\mu_{o2} \quad (13)$$

Since the physical characteristics of the oil and gas content in a given oil well do not alter rapidly, $\mu_{o1}$, $\mu_{o2}$, $\mu_{o3}$, $\mu_{g1}$, $\mu_{g2}$, $\mu_{g3}$, $\mu_{w1}$, $\mu_{w2}$, $\mu_{w3}$, can be considered to be constant for a considerably long period of time. $C_1$, $C_2$, $C_3$ can be determined by measuring the intensity of transmitted radiation, and $d_o \rho_o$, $d_w \rho_w$ and $d_g \rho_g$ can be found from the above equations, $d_o \rho_o$, $\rho_w \rho_w$ and $d_g \rho_g$ are, from their definitions, the sums of the mass of oil, water and gas each per unit area which extends across the transmission channel of radiation, over the whole length of the transmission channel of radiation. In summary, $d_o\rho_o$, $d_w\rho_w$ and $d_g\rho_g$ can be determined from the above equations if fixed values are given beforehand to $\mu_{w1}$, $\mu_{w2}$, $\mu_{w3}$, $\mu_{o1}$, $\mu_{o2}$, $\mu_{o3}$, $\mu_{g1}$, $\mu_{g2}$, $\mu_{g3}$ and $C_1$, $C_2$, and $C_3$ are determined by equations (4), (5), and (6) by measuring the intensity of transmitted radiation, so that the mass ratio of oil, water and gas in a crude oil stream can be measured on-line, the mass ratio of the oil, water and gas constituents can be determined. That is, since the intensity of transmitted gamma rays can be measured on-line without using any other information. This determination of mass ratio is not affected even if temperatures and pressure of crude oil alter and densities of gas, oil and water are changed.

EXAMPLE $Am_{241}$ is used as the radiation source. The source provides gamma rays of 59.5 keV and 26.8 keV, and x-rays of 13.9 keV, 17.8 keV and 20.8 keV. If we assume the radiation with energy under 26.8 keV to be x-rays at 20 keV, then by measuring gamma rays of 59.5 keV using a proportional counter tube as a pulse-counting-type radiation detector, the two energies can easily be separated and two intensities of gamma rays and x-rays can be measured simultaneously since energy resolution of a typical detector is about 10%. $Ga_{153}$ may be used as the radiation source which provides the third energy of radiation. The Ga emits gamma rays of about 100 keV. Measurement of the gamma rays can be performed using either a proportional counter tube or a scintillation detector.

If, for example the petroleum component is $C_nH_{2n}$ and the gas component is $CH_4$, the radiation mass absorption coefficients are as follows:

| $\mu_{o1}$ | $\mu_{o2}$ | $\mu_{o3}$ | $\mu_{w1}$ | $\mu_{w2}$ | $\mu_{w3}$ | $\mu_{g1}$ | $\mu_{g2}$ | $\mu_{g2}$ |
|---|---|---|---|---|---|---|---|---|
| 0.431 | 0.197 | 0.172 | 0.811 | 0.206 | 0.171 | 0.423 | 0.213 | 0.187 cm²/g. |

Therefore, $\mu_{o1}$, $\mu_{w1}$, $\mu_{g1}$ and $\mu_{o2}$, $\mu_{w2}$, $\mu_{g2}$ and $\mu_{o3}$, $\mu_{w3}$, $\mu_{g3}$ are linearly independent of one another, and $d_o\rho_o$, $d_w\rho_w$ and $d_g\rho_g$ can be independently determined, and the oil, water and gas constituents of crude oil can be determined. Since mass absorption coefficients are constants for the material, independent of temperature or pressure, mass constituents of oil, water and gas in crude oil can be obtained irrespective of the temperature or pressure of the crude oil.

An alternative system to that described above would be to use a detector system that can distinguish 3 energy levels from a single source such as $Am_{241}$.

Since during long periods of time, the properties of oil, water or gas may change, the arithmetic processor can be such as to be able to adjust the values of $\mu_{o1}$, $\mu_{o2}$, $\mu_{o3}$, $\mu_{w1}$, $\mu_{w2}$, $\mu_{w3}$, $\mu_{g1}$, $\mu_{g2}$ periodically.

Moreover, two separate radiation measuring systems can be used for the first and second types of radiation. In such case, a first radiation source, first radiation detector, first preamplifier and first main amplifier are used for the first type of radiation, and the second radiation source, second radiation detector, second preamplifier and second main amplifier are used for the second type of radiation. Alternatively, by utilizing a single pulse-counting-type detector for the three types of radiation, the radiation measuring system from the radiation detector to the main amplifier can be used in common by the radiation systems. An x-ray tube can be used in place of a gamma ray source. In the above example, measurement of the intensity of radiation is performed by a pulse counting method. It will be appreciated that the intensity of radiation can also be measured using a direct current-type detector. The signals proportional to the logarithm of the intensity of transmitted radiation are generated by the arithmetic processor. Such a measuring system can be designed to provide signals proportional to the logarithm of the intensity radiation by providing a logarithm counting-rate meter following the pulse-height discriminator.

By using beryllium as the material of the tube wall where radiation is being transmitted, attenuation of the radiation can be reduced and it is easier to measure transmitted radiation.

When fluctuations in the constituents of the crude oil are rapid, it is possible to automatically correct the detecting system. Such automatic correction can be made by providing a fourth radiation measuring system in which the photon energy of radiation is different from the photon energy of radiation in the first, second and third radiation measuring systems. For example, when the sulphur content of the crude oil fluctuates, a fourth radiation system is used to obtain the equation:

$$\mu_{o4}\rho_o d_o + \mu_{w4}\rho_w d_w + \mu_{g4}\rho_g d_g = \ln(I_{o4}/I_4) - \mu_4\rho d - \mu_{s4}w_s \quad (14)$$

where $w_s$ is the product of the sulfur density and the radiation distance in the sulfur component in the transmission channel, and the other symbols have the definitions given hereinbefore. It will be appreciated that $d_o\rho_o$, $d_w\rho_w$ and $d_g\rho_g$ and $w_s$ can be obtained by using the equations in which $\mu_{s1}w_s$, $\mu_{ss}w$, $\mu_{s3}w_s$ are subtracted from the right-hand-side of equations (1), (2), (3) respectively, and solving these equations and equation (14) simultaneously. In the case where the photon energy of the first, second and third levels of radiation are 20, 60 and 100 keV, the photon energy of the fourth source of gamma rays can be selected to be approximately 40 keV.

In the situation where it is desirable to correct the calculations to allow for fluctuations in the nickel content of the crude oil, a fifth radiation measuring system can be provided. The photon energy of the radiation is selected to differ sufficiently from the other photon energies that measurements can be made with sufficient accuracy. As above, when compensating for the sulphur content, the following equations are applicable when allowing for sulphur and nickel in the crude oil $$\mu_{o4}\rho_o d_o + \mu_{w4}\rho_w d_w + \mu_{g4}\rho_g d_g = \ln(I_{o4}/I_4) - \mu_4\rho d - \mu_{s4}w_s - \mu_{Ni4}w_{Ni} \quad (15)$$

$$\mu_{o5}\rho_o d_o + \mu_{w5}\rho_w d_w + \mu_{g5}\rho_g d_g = \ln(I_{o5}/I_5) - \mu_5\rho d - \mu_{s5}w_s - \mu_{Ni5}w_{Ni} \quad (816)$$

Again, similar versions of equations (1), (2) and (3) can be established and the 5 equations can be solved to obtain correct values of $d_o\rho_o$, $d_w\rho_w$ and $d_g\rho_g$.

Often crude oil contains sand. When the quantity of sand is small, $d_o\rho_o$, $d_w\rho_w$ and $d_g\rho_g$ can be determined in the manner described above in equations (1), (2) and (3). However, when the quantity of sand is large and fluctuates, the radiation sources should be selected to provide a fourth photon energy level such that $\mu_o$, $\mu_w$, $\mu_g$ and $\mu_{sD}$ for the 4 energies are linearly independent of each other. It is readily apparent that by solving the following equations, the proportions of oil, water, gas and sand can be obtained.

$$\mu_{o1}\rho_o d_o + \mu_{w1}\rho_w d_w + \mu_{g1}\rho_g d_g + \mu_{SD1}\rho_{SD} d_{SD} =$$
$$\ln(I_{o1}/I_1) - \mu_1 \rho d = a_1 - \ln I_1 \quad (17)$$

$$\mu_{o2}\rho_o d_o + \mu_{w2}\rho_w d_w + \mu_{g2}\rho_g d_g + \mu_{SD2}\rho_{SD} d_{SD} =$$
$$\ln(I_{o2}/I_2) - \mu_2 \rho d = a_2 - \ln I_2 \quad (18)$$

$$\mu_{o3}\rho_o d_o + \mu_{w3}\rho_w d_w + \mu_{g3}\rho_g d_g + \mu_{SD3}\rho_{SD} d_{SD} =$$
$$\ln(I_{o3}/I_3) - \mu_3 \rho d = a_3 - \ln I_3 \quad (19)$$

$$\mu_{o4}\rho_o d_o + \mu_{w4}\rho_w d_w + \mu_{g4}\rho_g d_g + \mu_{SD4}\rho_{SD} d_{SD} = \ln$$
$$(I_{o4}/I_4) - \mu_4 \rho d = a_4 - \ln I_4 \quad (20)$$

In the above equations the subscript SD is used to identify the values for sand.

By correlating the pressure drop values provided by the gauges 8 and 9 with the mass-ratio values obtained in the above described manner, mass flowrates for the various components are obtained from standard calibration correlations. Because of slippage in straight pipe flow there may be significant differences between the flow velocities in the various phases. A flow restriction promotes equalized flow velocities of the components in the region of the restriction and flowrates.

The technique described above uses gamma/x-rays of low energy in order to distinguish between the water and oil components, and the technique is thus practically limited to internal piper diameters (or path length in the fluid) of about 1 to 10 cm. Production pipeline diameters are, however, generally in the range of 5 cm to 20 cm in diameter. In order to use this technique then in a production system, the production pipe diameter may be reduced at the measurement point to enable or improve the accuracy of measurement of the component fractions, this also providing, through the pressure drop measurement through the flow restriction, the means to convert the mass fractions of the components to mass flowrate.

Hence the combination of the low energy radiation method with a measurement in the reduced diameter of a choke provides the required sensitivity for the determination of the separate components with high accuracy.

What we claim is:

1. A method of measuring the proportions of various components in a crude oil mixture flowing through a pipeline comprising the steps of irradiating said mixtures with gamma rays or x-rays of at least three distinct energy levels; detecting the gamma rays or x-rays of at least three distinct energy levels passing through a known volume of the mixture to generate at least three signals proportional to said components in the mixture; processing said signals to obtain a mass ratio of the components; measuring the temperature of the mixture; measuring the pressure drop of the mixture through a flow restriction; and correlating the mass ratio, temperature and pressure drop values and standard calibration correlations previously prepared to obtain a mass flow rate of each of the components present in the mixture.

2. A method according to claim 1, wherein said irradiating step is performed in the flow restriction.

3. An apparatus for measuring the proportions of various components in a crude oil mixture flowing in a pipeline comprising a choke means for restricting the flow of a mixture along a predetermined length of the pipeline; a source of radioactivity for irradiating the mixture in the area of said choke means with gamma rays or x-rays of at least three distinct energy levels; detector means for detecting the gamma rays or x-rays of at least three distinct energy levels transmitted by the components of said mixture to generate a first set of signals, pressure measuring means for measuring the pressure drop of said mixture across said choke means to generate a second set of signals; and signal processor means for correlating the first and second set of signals and standard calibration correlations previously prepared to provide a mass flow rate for the mixture indicative of the relative proportions of each of the components of the mixture.

4. An apparatus according to claim 3, wherein said source of radioactivity and said detector means are located in said choke means.

5. An apparatus according to claim 4, including temperature gauge means for measuring the temperature of the mixture in the area of said choke means to generate a third set of signals for correlation with said first and second set of signals.

6. An apparatus according to claim 3, wherein said choke means is variable for changing the size of the restriction on the flow of the mixture.

7. An apparatus according to claim 4, wherein said choke means is variable for changing the size of the restriction on the flow of the mixture.

8. An apparatus according to claim 5, wherein said choke means is variable for changing the size of the restriction on the flow of the mixture.

* * * * *